United States Patent [19]
Robinson

[11] Patent Number: 5,874,495
[45] Date of Patent: Feb. 23, 1999

[54] POLYMERS USEFUL AS PH RESPONSIVE THICKENERS AND MONOMERS THEREFOR

[75] Inventor: Fred Robinson, Newton, Pa.

[73] Assignee: Rhodia Inc., Cranbury, N.J.

[21] Appl. No.: 487,755

[22] Filed: Jun. 7, 1995

Related U.S. Application Data

[63] Continuation of Ser. No. 317,261, Oct. 3, 1994, abandoned.

[51] Int. Cl.$^6$ ............... C08K 5/09; C08K 5/10; C08K 220/18; C08K 220/30
[52] U.S. Cl. ............ 524/300; 526/320; 526/318.4; 526/318.44; 526/329.3; 526/932; 524/317
[58] Field of Search .............................. 524/300, 317; 526/320, 318.4, 318.44, 318.25, 329.3, 932

[56] References Cited

U.S. PATENT DOCUMENTS

| | | | |
|---|---|---|---|
| 3,652,497 | 3/1972 | Jones et al. | 260/47 |
| 3,657,175 | 4/1972 | Zimmerman | 260/296 |
| 3,891,591 | 6/1975 | Chang et al. | 260/296 |
| 4,075,411 | 2/1978 | Dickstein | 560/224 |
| 4,079,028 | 3/1978 | Stevens | 260/29.6 |
| 4,138,381 | 2/1979 | Chang et al. | 524/765 |
| 4,155,892 | 5/1979 | Stevens | 260/29.2 |
| 4,268,641 | 5/1981 | Koenig et al. | 525/367 |
| 4,384,096 | 5/1983 | Sonnablend | 526/313 |
| 4,421,902 | 12/1983 | Chang et al. | 526/317 |
| 4,469,611 | 9/1984 | Snyder, Jr. et al. | 252/75 |
| 4,639,395 | 1/1987 | Clarke et al. | 428/341 |
| 4,668,410 | 5/1987 | Haas et al. | 252/49.3 |
| 4,741,790 | 5/1988 | Hawe et al. | 156/71 |
| 4,769,167 | 9/1988 | Haas et al. | 252/76 |
| 4,814,000 | 3/1989 | Ciocca et al. | 71/111 |
| 4,814,514 | 3/1989 | Yokata et al. | 568/608 |
| 4,912,245 | 3/1990 | Giardeau et al. | 558/118 |
| 4,921,902 | 5/1990 | Evani et al. | 524/555 |
| 5,015,711 | 5/1991 | Simonet et al. | 526/301 |
| 5,082,591 | 1/1992 | Marchetto | 568/608 |
| 5,086,142 | 2/1992 | Fock et al. | 526/318 |
| 5,192,592 | 3/1993 | Shay | 427/358 |
| 5,294,693 | 3/1994 | Egraz et al. | 526/310 |
| 5,362,415 | 11/1994 | Egraz et al. | 526/310 |

FOREIGN PATENT DOCUMENTS

| | | | |
|---|---|---|---|
| 1188043 | 5/1985 | Canada | C08F 220/06 |
| 0 003 235 | 8/1979 | European Pat. Off. | C08F 220/28 |
| 0 013 836 | 8/1980 | European Pat. Off. | C08F 220/28 |
| 0 190 892 | 8/1986 | European Pat. Off. | C08F 2/221 |

*Primary Examiner*—Jeffrey T. Smith
*Assistant Examiner*—Wu C. Cheng
*Attorney, Agent, or Firm*—John Daniel Wood; Anthony Venturino; Paul J. Juettner

[57] ABSTRACT

Novel aqueous thickener or thixotropic polymers are prepared by the copolymerization of (A) about 15–60 weight percent of a $C_3$–$C_8$ alpha, beta-ethylenically unsaturated carboxylic acid monomer, preferably acrylic or methacrylic acid or a mixture thereof with itaconic or fumaric acid, (B) about 15–80 weight percent of a nonionic copolymerizable $C_2$–$C_{12}$ alpha, beta-ethylenically unsaturated monomer, preferably a monovinyl ester such as ethyl acrylate or a mixture thereof with styrene, acrylonitrile, vinyl chloride or vinyl acetate, and (C) about 1–30 weight percent of a new and novel nonionic ethylenically unsaturated nonionic biphillic monomer such as tristyrylpoly(ethyleneoxy)$_x$ methyl acrylate, to provide a stable aqueous colloidal dispersion at an acid pH lower than about 5.0 but becoming an effective thickener for aqueous systems upon adjustment to a pH of about 5.5–10.5 or higher. These polymers adjusted to a pH of about 5.5 or higher are effective thickeners for a wide variety of aqueous systems including cosmetic products, drilling muds, aqueous coating compositions such as latex paint, and high solids compositions such as spackle, grouts, cements, and the like.

22 Claims, No Drawings

POLYMERS USEFUL AS PH RESPONSIVE THICKENERS AND MONOMERS THEREFOR

This is a continuation of application Ser. No. 08/317,261 filed on Oct. 3, 1994, now abandoned.

BACKGROUND OF THE INVENTION

Polymeric water-soluble thickening agents have been extensively used for thickening aqueous based systems containing electrolytes or a dispersed phase including coatings, e.g., latex paints, printing pastes for textiles, bleaching agents, alkaline liquors or paint removers as well as high solids content products like spackle, cements, grout and the like. Further important applications relate to the production of petroleum and ores, as filtration aids or flocculents, and found use in working fluids such as hydraulic fluids and metal working fluids.

In aqueous coating compositions, such as latex paints, it is important to control the rheology to obtain proper flow and leveling with a minimum of dripping and spattering. In other compositions Newtonian flow thickeners are required because of the high shear involved in their use.

Cellulose ethers, alkali soluble latex copolymers, copolymers of acrylic and methacrylic acids and esters which have a portion of the hydrogen ions of the copolymer carboxyl groups replaced with ammonium or alkali metal ions have been used as thickeners as well as other types of polymeric thickeners which contain various carboxylic acid groups which can be solubilized in water by neutralization with a water-soluble base.

A solid styrene-maleic anhydride-vinylbenzyl ether terpolymer soluble at high pH and useful as a thickener for aqueous solutions, in spite of excellent rheology, has had limited use as a paint thickener because of stability problems and cost.

U.S. Pat. No. 4,384,096 discloses a pH responsive thickener comprising an ethylenically unsaturated carboxylic acid, at least one ethylenically unsaturate monomer, and an ethylenically unsaturated surfactant copolymerizable therewith. The surfactant is an alkylphenoxypoly(ethyleneoxy) ethyl acrylate. Similar systems are disclosed in U.S. Pat. Nos. 4,138,381; 4,268,641; 4,668,410; 4,769,167; 5,086,142; and 5,192,592.

It is also known that water soluble polymers of the same type as disclosed in the preceding patents can be used in the formulation of synthetic and semi-synthetic hydraulic fluids to adjust the viscosity to the proper level to achieve technical requirements. See U.S. Pat. Nos. 4,668,410 and 4,769,167.

SUMMARY OF THE INVENTION

In accordance with the invention, there is provided a new and novel copolymerizable nonionic ethylenically unsaturated biphilic monomer which can be used in preparing stable liquid emulsion or solution polymers having low viscosity and relatively high solids content under acidic conditions which become very efficient polymeric thickeners for many aqueous systems when treated with base. These new polymers, which surprising develop maximum viscosity at lower pHs than similar products presently available in the prior art, can be prepared in the form of an aqueous colloidal dispersion of water-insoluble polymer by emulsion polymerizing at a Ph of about 2.5 to 5.0 three ethylenically unsaturated monomeric components: (A) a carboxylic acid monomer, (B) a nonionic vinyl monomer and (C) the novel nonionic ethylenically unsaturated biphilic monomer of the invention.

The emulsion polymerization is normally carried out under acidic conditions in which the carboxylic acid groups are in protonated form to insolubilize the polymer and give a liquid emulsion. The finely divided polymer particles in such a liquid colloidal dispersion dissolve almost instantly upon pH adjustment. The ease of handling, metering, and dispersing the liquid emulsion polymer, the rapid solubilization by controlled pH adjustment, and the highly desirable Theological properties make this liquid emulsion polymer a most effective and efficient thickening agent for a wide variety of applications including latex paints and other aqueous coating and heavy solids compositions.

DETAILED DESCRIPTION OF THE INVENTION

The novel liquid emulsion polymers of this invention are prepared from three basic components: (A) an $C_3$–$C_8$ alpha, beta-ethylenically unsaturated carboxylic acid monomer, (B) a copolymerizable nonionic vinyl monomer, and (C) certain new and novel copolymerizable nonionic ethylenically unsaturated biphilic monomers. The effectiveness of these liquid emulsion polymers as a pH responsive thickener for many aqueous products is dependent on these components in that the acid component A provides the requisite pH responsiveness; the nonionic vinyl comonomer B provides an extended polymer backbone and added hydrophilic lipophilic balance; and the novel ethylenically unsaturated nonionic biphilic monomers C provides an in situ, bound surfactant to control the rheology of the aqueous system containing the solubilized polymeric thickener. The proportions of the individual monomers can be varied to achieve optimum properties for specific applications.

The new and novel copolymerizable ethylenically unsaturated nonionic surfactant of the invention can be represented by the formula:

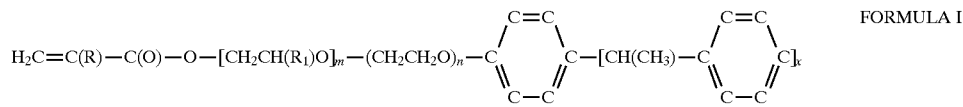

FORMULA I where R is H or $CH_3$; $R_1$ is $C_1$–$C_4$ alkyl; n is an average number from about 6–100 and m is an average number from about 0–50 provided that n is > or =m and SIGMA (n+m) is about 6–100, and x is an average number of from about 2 to about 3, wherein the substituent denoted x is randomly distributed around the benzene ring to which it is attached.

The preferred surfactants are the acrylate and methacrylate esters which include (1-phenyl ethyl)$_x$ phenyl poly (alkyleneoxy) (meth)acrylates where x is a number of from about 2–3, and the poly(alkyleneoxy) moiety is preferably ethyleneoxy though it can be ethyleneoxy and/or propyleneoxy, the repeating alkyleneoxy units being a number average of from about 6–100. An alternate name for the (1-phenyl ethyl) phenyl group is the mono, di or tristyrylphenol.

The new and novel ethylenically unsaturated nonionic biphilic monomers of the invention are the acrylic or methacrylic acid esters of certain nonionic surfactant alcohols.

Such surfactant alcohols are known in the art, e.g. U.S. Pat. No. 5,082,591. The alcohols can be prepared by alkoxylating a styrylphenol by known methods. For example, the alcohols can be prepared by the reaction of at least one poly(1-phenyl ethyl)$_x$ phenol wherein x is an average of 2–3 with a mixture of monoethylene glycol and monopropylene glycol. If organic solvent solubility is desired, the ratio of the monoethylene glycol to monopropylene glycol ranging from about 75/25 to 90/10 and preferably from about 80/20 to 90/10 is taught as necessary. This is more fully disclosed in U.S. Pat. No. 5,082,591, the disclosure of which is incorporated herein by reference.

The reaction can be carried out for a period of time sufficient for reaction, e.g., from about 20 to 40 minutes, at a temperature ranging from about 140° to 180° C., in the presence of from about 0.5 to 1.5% by weight with respect to the finished product of an alkaline base, such as soda, as a catalyst. The (1-phenyl ethyl)$_x$ phenol together with the glycol(s) are used in substantially stoichiometric amounts. Variations in reaction conditions would be obvious to one of ordinary skill in the art as would other methods of preparing the compounds of the invention. Additional surfactant alcohols which can be esterified for use herein are given in "McCutcheon's Detergents and Emulsifiers" 1973, North American Edition, Allured Publishing Corp., Ridgewood, N.J. 07450 under the trademark SOPROPHOR offered by Rhone-Poulenc.

The tristyrylphenol alkoxylate can then be esterified with an ethylenically unsaturated carboxylic acid or its anhydride by known methods to obtain the desired product, e.g., U.S. Pat. No. 4,075,411.

The novel surfactants of the invention can be prepared by the direct acid catalyzed esterification of the appropriate surfactant alcohol with an excess of the carboxylic acid monomer used as Component A in the formation of the final polymer. The resulting mixture with excess acid can be used directly in the copolymerization provided that at least 30 percent, and preferably 50–70 percent or more, of the surfactant alcohol in the mixture is esterified. The novel surfactants of the invention can also be recovered, purified by conventional means using an appropriate inhibitor such as hydroquinone or p-tert-butylcatechol to prevent undesired homopolymerization, and then used to prepare the liquid emulsion polymers.

It has been found that the hydrophilic lipophilic balance (HLB) of the novel surfactants of the invention is an important factor in the performance of the resulting emulsion polymer. Thus for a given polyethyleneoxy content, increasing the molecular weight of the terminal hydrophobic group will increase the efficiency of the resulting polymer as a thickener. Also for a given lipophilic group decreasing the number of polyethyleneoxy groups increases thickener efficiency. For many surfactant esters usable herein an average of about 10–40 ethyleneoxy groups (e.g., In Formula I, m=0, and n=10–40) is preferred.

The ethylenically unsaturated nonionic biphillic monomer is generally used in the copolymer in an amount ranging from about 1 to about 30 (preferably from about 1–20, and more preferably from about 1–12) weight percent based on the total weight of the monomers present.

The liquid emulsion polymer requires from about 15–60 weight percent based on total monomers of a $C_3$–$C_8$ alpha, beta-ethylenically unsaturated carboxylic acid monomer of the formula:

$$RCH{=}C(R_1){-}C(O)OH \qquad \text{FORMULA II}$$

where when (a) R is H then $R_1$ is H, $C_1$–$C_4$ alkyl, or —CH$_2$C(O)OX; (b) R is —C(O)OX then $R_1$ is H or —CH$_2$C(O)OX; or R is CH$_3$ then $R_1$ is H; and X is H or $C_1$–$C_4$ alkyl.

Acrylic or methacrylic acid or a mixture thereof is preferred though these acids can be used with minor proportions of itaconic or fumaric acid, crotonic and aconitic acid and half esters of these and other polycarboxylic acids such as maleic acid with $C_1$–$C_4$ alkanols. It is preferable to have at least about 25 weight percent, more preferably from about 30–55 and most preferably from about 30–45 weight percent of the carboxylic acid monomer in the polymer though polycarboxylic acid monomers and half esters can be substituted for a portion of the acrylic or methacrylic acid, e.g., about 1–15 weight percent based on total monomers.

To provide the extended polymer backbone and body needed for effective thickening requires about 15–80 weight percent of at least one copolymerizable nonionic $C_2$–$C_{12}$ alpha, beta-ethylenically unsaturated monomer selected from the group consisting of the formula:

$$CH_2{=}CYZ \qquad \text{FORMULA III}$$

wherein when Y is H then Z is —COOR', —C$_6$H$_4$R", CN, Cl, —OC(O)R''' or —CH=CH$_2$; when Y is CH$_3$ then Z is —COOR', —C$_6$H$_4$R", CN or —CH=CH$_2$; or when Y is Cl then Z is Cl; and R' is $C_1$–$C_8$ alkyl or $C_2$–$C_8$ hydroxyalkyl; R" is H, Cl, Br, or $C_1$–$C_4$ alkyl; R''' is $C_1$–$C_8$ alkyl.

Typical of such monomers are the $C_1$–$C_8$ alkyl and $C_2$–$C_8$ hydroxyalkyl esters of acrylic and methacrylic acid including ethyl acrylate, ethyl methacrylate, methyl methacrylate, 2-ethylhexyl acrylate, butyl acrylate, butyl methacrylate, 2-hydroxyethyl acrylate, 2-hydroxybutyl methacrylate; styrene, vinyltoluene, t-butylstyrene, isopropylstyrene, and p-chlorostyrene; vinyl acetate, vinyl butyrate, vinyl caprolate; acrylonitrile, methacrylonitrile, butadiene, isoprene, vinyl chloride, vinylidene chloride, and the like. In practice, a monovinyl ester such as ethyl acrylate or a mixture thereof with styrene, hydroxyethyl acrylate, acrylonitrile, vinyl chloride or vinyl acetate is preferred.

Normally from about 15–80 weight percent, and preferably from about 35–70 and more preferably from about 50–70 weight percent of nonionic vinyl monomer, based on total weight of monomers, is used in preparing the liquid emulsion polymer.

The hydrophilic balance of the copolymer product can be adjusted to a degree by the judicious selection of the nonionic vinyl monomer B; e.g., a soft, (1-phenyl ethyl) phenylpoly(ethyleneoxy)ethyl ester can be used in a system with mixture of ethyl acrylate and a hard comonomer such as styrene. It is critical to the performance of these products that they contain an effective amount of an in situ, bound surfactant to control the rheology of the aqueous system thickened with the solubilized emulsion polymer.

2. Copolymerization

The liquid emulsion copolymers of the invention can be conveniently prepared from the above-described monomers by conventional emulsion polymerization techniques at an acid pH lower than about 5.0 using free-radical producing initiators, usually in an amount from 0.01 percent to 3 percent based on the weight of the monomers. Polymerization at an acid pH lower than about 5.0 permits direct preparation of an aqueous colloidal dispersion with relatively high solids content without problems of undue viscosity. The free-radical producing initiators conveniently are peroxygen compounds especially inorganic persulfate compounds such as ammonium persulfate, potassium persulfate, sodium persulfate; peroxides such as hydrogen peroxide; organic hydroperoxides, for example, cumene hydroperoxide, t-butyl hydroperoxide; organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite); as well as other free-radical producing materials such as 2,2'-azobisisobutyronitrile and high radiation sources.

Optionally, a chain transfer agent and an additional emulsifier can be used. Representative chain transfer agents are carbon tetrachloride, bromoform, bromotrichloromethane, long chain alkyl mercaptans and thioesters such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate. The chain transfer agents can be used in amounts up to about 10 parts per 100 parts of polymerizable monomers.

At least one anionic emulsifier can also be included in the polymerization charge and one or more of the known nonionic emulsifiers may also be present. Examples of anionic emulsifiers are the alkali metal alkyl aryl sulfonates, the alkali metal alkyl sulfates and the sulfonated alkyl esters. Specific examples of these well-known emulsifiers are sodium dodecylbenzenesulfonate, sodium disecondary-butylnaphthalene sulfonate, sodium lauryl sulfate, disodium dodecyldiphenyl ether disulfonate, disodium n-octadecylsulfosuccinamate and sodium dioctylsulfosuccinate.

Optionally, other ingredients well known in the emulsion polymerization art may be included such as chelating agents, buffering agents, inorganic salts and pH adjusting agents.

Usually the copolymerization is carried out at a temperature between about 60° C. and 90° C. but higher or lower temperatures may be used. The polymerization can be carried out batchwise, stepwise or continuously with batch and/or continuous addition of the monomers in a conventional manner.

The monomers can be copolymerized in such proportions, and the resulting emulsion polymers can be physically blended, to give products with the desired balance of properties for specific applications. For example, if a more viscous product is desired, the acid and surfactant monomer content can be increased. Greater flexibility and coalescence can be obtained with higher amounts of ethyl acrylate. Addition of styrene as a second nonionic vinyl monomer will increase to a higher pH the adjustment required to dissolve the emulsion in an aqueous coating composition. Minor quantities of a polyfunctional monomer, such as itaconic or fumaric acid or isoprene to introduce a higher carboxylic acid content or limited crosslinking, provides further control on the solubility of the emulsion polymer after pH adjustment. Thus, by varying the monomers and their proportions, emulsion polymers having optimum properties for particular applications can be designed. Particularly effective liquid emulsion polymer thickeners are obtained by copolymerization of about 40–50 weight percent of methacrylic acid, about 35–50 weight percent of ethyl acrylate, and about 1–12 weight percent of the methacrylic ester of a $C_9$-alkylphenoxy(ethyleneoxy)$_9$ ethyl alcohol.

As the tristyrylethoxylate methacrylates of the invention have increased chain transfer ability, it may be desirable to add a polyfunctional monomer, e.g., diallyl phthalate, and closely control the polymerization to increase viscosity.

The copolymer products prepared by emulsion polymerization at an acid pH are in the form of stable aqueous colloidal dispersions containing the copolymer dispersed as discrete particles having average particle diameters of about 500–3000 A, preferably about 1000–1750 A, as measured by light refraction. Dispersions containing polymer particles smaller than about 500 A are difficult to stabilize while particles larger than about 3000 A reduce the ease of dispersion in the aqueous products to be thickened.

These emulsion copolymers will normally have number average molecular weights of at least about 30,000 daltons as determined by gel permeation chromatography. To provide most effective thickening with copolymers which are water-soluble when neutralized, molecular weights within the range of about 200,000 to 5,000,000 daltons are preferred. In terms of a standard Brookfield viscosity measured as a 1 percent aqueous solution in ammonium salt form at pH 9 and 25° C., a copolymer with a viscosity of about 50–50,000 cps, and preferably about 100–30,000 cps, is particularly desirable for many applications. The aqueous dispersions of the copolymers contain about 10–50 weight percent of polymer solids and are of relatively low viscosity. They can be readily metered and blended with aqueous product systems.

The dispersions are pH responsive. When the pH of the polymer dispersion is adjusted by addition of a base such as ammonia, an amine or a non-volatile inorganic base such as sodium hydroxide, potassium carbonate or the like, the aqueous mixture becomes translucent or transparent as the polymer dissolves at least partially in the aqueous phase with a concurrent increase in viscosity.

This neutralization can occur in situ when the liquid emulsion polymer is blended with an aqueous solution containing a suitable base. Or if desired for a given application, pH adjustment by partial or complete neutralization can be carried out before or after blending the liquid emulsion polymer with an aqueous product.

The term "liquid emulsion polymer" as applied to the new thickener of this specification means that the thickener is an emulsion polymer because the polymer was prepared by emulsion polymerization even though the polymer per se may be (and generally is) a solid at room temperature but is a "liquid" emulsion polymer because it is in the form of a liquid solution or dispersion.

The pH viscosity response curves for several typical liquid emulsion polymers prepared by copolymerizing methacrylic acid (MAA), ethyl acrylate (EA), and nonylphenoxypoly (ethyleneoxy) 9ethyl methacrylate (VSE-1A) are shown in the FIGURE as determined in aqueous media at a concentration of 1 percent by weight and at room temperature. Note that the pH range of initial viscosity build can be controlled by variation in the composition of the emulsion copolymer.

Polymers can also be made using solution polymerization techniques well known to those of skill in the art. The monomers can be dissolved in an appropriate solvent such as toluene, xylene and tetrahydro furan. Polymerization can be accomplished in the time and at the temperature necessary, e.g., 60°–80° C. and 8–24 hours. The product can be worked up through normal techniques including solvent stripping.

The polymers prepared in accordance with the invention are useful as water-soluble thickeners for a wide variety of applications ranging from cosmetics to drilling muds, but particularly for aqueous coating compositions. Solution polymerized polymers can be used in solvent systems or emulsified by known techniques for use in aqueous systems.

The liquid emulsion polymers described herein are particularly useful as thickeners for a wide variety of water-based compositions including aqueous brine and polymer solutions as well as aqueous slurries and colloidal dispersions of water-insoluble inorganic and organic material including compositions such as natural rubber, synthetic or artificial latexes and aqueous products containing such materials. The emulsion polymers of the invention are especially useful in areas requiring thickening at pHs near neutral such as in cosmetics. The compositions of the invention can provide substantially maximum thickening at neutral pH whereas many of the compositions of the prior art require alkaline pH for maximum thickening.

Synthetic latexes which may be thickened with the liquid emulsion polymers are aqueous colloidal dispersions of water-insoluble polymers prepared by emulsion polymerization of one or more ethylenically unsaturated monomers. Typical of such synthetic latexes are emulsion copolymers of monoethylenically unsaturated compounds such as styrene, methyl methacrylate, acrylonitrile with a conjugated diolefin such as butadiene or isoprene; copolymers of styrene, acrylic and methacrylic esters, copolymers of vinyl halide, vinylidene halide, vinyl acetate and the like. Many other ethylenically unsaturated monomers or mixtures thereof can be emulsion polymerized to form synthetic latexes.

The thickeners of this invention are advantageous for use with the water-based compositions according to the foregoing description and with compositions containing those materials, especially coating compositions of various types. Mixtures of two or more thickeners may be used, if desired. Of course the latex polymers used in coating compositions are preferably film-forming at temperatures below about 25° C., either inherently or through the use of plasticizers. Such coating compositions include water-based consumer and industrial paints; sizing, adhesives and other coatings for paper, paperboard, textiles; and the like.

Usually these latex coating compositions contain added pigments, fillers and extenders such as titanium dioxide, barium sulfate, calcium carbonate, clays, mica, talc, silica and the like. The novel liquid emulsion polymers described herein are compatible with most latex paint systems and provide highly effective and efficient thickening. Suitable results are obtained using about 0.05–5.0 weight percent of the liquid emulsion polymer based on total weight of solids, and preferably about 0.1–2.0 weight percent.

The aqueous compositions thickened with the liquid emulsion polymers of this invention preferably are those in which any dispersing or solvating liquid present consists of greater than 50 percent by weight of water.

The following examples illustrate further the present invention. Unless otherwise indicated, all parts and percentages are by weight.

EXAMPLE 1

Preparation of Tristyrylphenol Ethoxylate

Typically tristyrylphenyl ethoxylate can be prepared by reacting tristyrylphenol and soda with monoethylene &/or monopropylene glycol at a temperature and time sufficient to allow alkoxylation, e.g., 160° C. for about 30 minutes. The tristyrylphonol and the monoalkylene glycols are used in stoichiometric amounts, the ratio of ethylene to propylene glycol being that desired for the final desired ratio. The tristryrlphenol as used is a mixture of mono, di and tristyryl compounds with the tristyryl moiety prevailing.

Preparation of Biphilic Monomer 1A

The following is a procedure for the preparation of the ethylenically unsaturated nonionic biphilic monomer of the invention.

The biphilic monomer can be prepared by charging a 3 liter four neck round bottom flask equipped with a heater, thermometer, subsurface air sparge (about 100 milliliters/minute), an addition funnel, and a stirrer with 1508.04 grams of tristyrylphenol ethoxylate (EO=25) available as SOPROPHOR S/25 from Rhône-Poulenc Inc. which had been previously liquified in a 60° C. oven. 500 ppm methyl hydroquinone was also charged at that point. The water content was maintained at less than 0.1%. The temperature was elevated to about 60° C. with air sparging and stirring. 154.17 grams of methacrylic anhydride was incrementally added maintaining the reaction temperature between 60° and 90° C. After addition was completed, samples were analyzed until the IR peak at 1780 cm$^{-1}$ corresponding to methacrylic anhydride was minimized and the acid number was stable. The final product, 1576.11 grams, was stored in an amber jar.

Preparation of Biphilic Monomer 1B

The biphillic monomer 1B can be prepared by charging a 1 liter four neck round bottom flask equipped with a heater, thermometer, subsurface air sparge (about 100 milliliters/minute), an addition funnel, and a stirrer with 500 grams of tristyrylphenol ethoxylate (EO=16) available as SOPROPHOR 37 from Rhône-Poulenc Inc. and 500 ppm methyl hydroquinone. The water content was maintained at less than 0.1%. At a temperature of about 25° C. with air sparging and stirring, 84.42 grams of methacrylic anhydride was incrementally added. No increase in reaction temperature was noted. After addition was complete, the temperature was elevated to 50° C. Samples were analyzed until the methacrylic anhydride was minimized and the acid number was stable (about 12 hours). The final product was cooled and stored in an amber jar.

Preparation of Biphilic Monomer 1C

The process used to prepare sample 1C was repeated using 301 grams of tristyrylphenol ethoxylate (EO=40) available as SOPROPHOR 40 from Rhône-Poulenc Inc. and 105.9 grams of methacrylic acid.

EXAMPLE 2

An emulsion polymer utilizing the biphilic monomer of the invention was prepared as follows.

An emulsion of monomers was prepared by mixing 153.4 grams of ethyl acrylate, 100.9 grams of methacrylic acid, 6.6 grams of a solution containing 58.9 weight % of the monomer prepared in Example 1, 20 weight % methacrylic acid and 20 weight % water, 12.0 grams of Abex EP 100 (nonylphenol polyethoxylate ammonium salt), 0.4 grams of diallyl phthalate and 150 grams of deionized water.

To a one liter externally heated/cooled glass reactor equipped with an agitator and feed pumps were added 291 grams of deionized water and 1.0 grams of Abex EP 100 under a nitrogen blanket. The vessel was heated to 84°–86° C. and 10 grams of the above described emulsion and 2.5 grams of a 0.56% solution of ammonium persulfate was added. After evidence of polymerization was noted (0.5 to 2.0 minutes), the remaining monomer emulsion along with 30 grams of a 1.27% solution of ammonium persulfate was added incrementally over 90 minutes. The reaction temperature was maintained at 84°–86° C. with external cooling. After the addition of the reactants, the reactor was heated to 90° C. for 30 minutes. The reactor was then cooled to 62°–64° C. and 30 grams of a 1.8% aqueous solution of t-butyl hydroperoxide and 30 grams of a 0.36% aqueous solution of erythorbic acid was added in three equal increments 20 minutes apart. The reactor temperature was held at 63°–65° C. for 45 minutes. The resultant latex was filtered through a 250 mesh screen and then a 325 mesh screen to provide a polymer emulsion containing approximately 59% ethyl acrylate, 39.35% methacrylic acid, 1.5% biphilic monomer and 0.15% diallyl phthalate.

The latex was subsequestly neutralized and dissolved to 1% solids by weight. The transformation from a lates to a medium viscosity clear solution occurred near pH6 and maximum viscosity was obtained at about pH 7.5.

Other polymers were prepared using the same procedure with the following monomer charges:

| Sample | Ethyl Acrylate | Methacrylic Acid | Biphilic of Example 1 | Diallyl Phthalate |
|---|---|---|---|---|
| A. | 59% | 36.00% | 5.0% (IA) | — |
| B. | 59% | 38.00% | 3.0% (IA) | — |
| C. | 59% | 39.35% | 1.5% (IB) | 0.15 |
| D. | 59% | 36.00% | 5.0% (IC) | — |

EXAMPLE 3

The thixotropic behavior of aqueous solutions of copolymers prepared using the biphilic monomer of the invention can be shown by the following:

To a 250 milliliter beaker equipped with a magnetic stirrer are added 6.67 grams of a 30% solids latex and 191.88 grams of deionized water. 1.35 grams of caustic (25% NaOH) was added dropwise until the desired pH was attained (by pH meter). When the solution clears and is at the desired pH (pH 7–7.5), the solution is stirred at 25° C. for about 2 hours to insure uniformity. The viscosity is determined with a model LVT Brookfield Viscometer using a #3, 4, or 5 spindle at 3, 6, 12, 30, and 60 RPM. The following results were obtained:

Sample 3A

59% ethyl acrylate, 39.35% methacrylic anhydride, 1.5% tristyrylphenol (ethoxylate)$_{25}$ methacrylate and 0.15% diallyl phthalate.

TABLE

| pH | 3 RPM | 6 RPM | 12 RPM | 30 RPM | 60 RPM |
|---|---|---|---|---|---|
| 7.06 | 10998 | 6199 | 3749 | 2020 | 1270 |
| 8.04 | 8998 | 5599 | 3499 | 1960 | 1280 |
| 9.36 | 8798 | 5499 | 3399 | 1907 | 1220 |

Sample 3B

59% ethyl acrylate, 36% methacrylic acid, 5 % tristyrylphenol (ethoxylate)$_x$ methacrylate at a pH of about 7:

| x | 6 RPM | 12 RPM | 30 RPM | 60 RPM |
|---|---|---|---|---|
| 16 | 2100 | 1670 | 1044 | 728 |
| 25 | 2060 | 1580 | 1052 | 746 |

A latex was prepared according to the process outlined in Example 2 using a behenyl ethoxylate$_{25}$ methacrylate(BEM) or a tristyrylphenol ethoxylate$_{25}$ methacrylate. The thickening ability of 1% solutions at a pH of about 7 were compared using the procedure outlined hereinbefore with the following results:

| MONOMER | 6 RPM | 12 RPM | 30 RPM | 60 RPM |
|---|---|---|---|---|
| Inv. x = 25 | 4439 | 2779 | 1540 | 1002 |
| BEM | 1340 | 1410 | 1520 | 1424 |

Additional advantages and modifications will be readily apparent to those skilled in the art. Accordingly, variations can be made without departing from the spirit and general inventive concept as defined in the appended claims and their equivalents.

What is claimed is:

1. A liquid emulsion polymer useful as a pH responsive thickener for aqueous compositions comprising an aqueous emulsion copolymer of:

A. about 15–60 weight percent based on total monomers of at least one $C_3$–$C_8$ alpha, beta-ethylenically unsaturated carboxylic acid monomer;

B. about 15–80 weight percent of at least one nonionic, copolymerizable $C_2$–$C_{12}$ alpha, beta-ethylenically unsaturated monomer of the formula:

$$CH_2=CYZ(II) \qquad \text{Formula III.}$$

where Y is H, Z is —COOR', —$C_6H_4R''$, CN, Cl, —OC(O)R''' or —CH=$CH_2$; Y is $CH_3$ and Z is —COOR', —$C_6H_4R''$, CN or —CH=$CH_2$; or Y and Z are Cl; and R' is $C_1$–$C_8$ alkyl or $C_2$–$C_8$ hydroxyalkyl; R'' is H, Cl, Br, or $C_1$–$C_4$ alkyl; and R''' is $C_1$–$C_8$ alkyl; and C. about 1–30 weight percent based on total monomers of at least one nonionic ethylenically unsaturated biphilic monomer of the formula:

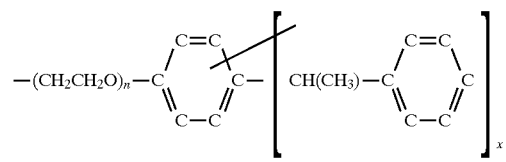

Formula I.

wherein R and $R_1$ represent hydrogen or methyl, n is an average number from about 6 to about 100, m is an average number of from about 0–50 provided that n is > or =m and SIGMA (m+n) is an average number from about 6–100, and x is an average number of from about 2 to about 3, said polymer being stable as an aqueous colloidal dispersion at a pH lower than about 5.0 but becoming an effective thickener for aqueous systems upon adjustment to a pH of about 5.5–10.5 or higher.

2. A polymer of claim 1 where the carboxylic acid monomer (A) is methacrylic acid, acrylic acid, or a mixture thereof with fumaric or itaconic acid.

3. A polymer of claim 1 containing about 30–55 weight percent of methacrylic acid or a mixture thereof with a minor amount of itaconic acid.

4. A polymer of claim 1 where the comonomer (B) is a monovinyl ester or a mixture thereof with styrene, 2-hydroxyethyl acrylate, acrylonitrile, vinyl chloride or vinyl acetate.

5. A polymer of claim 1 where the comonomer (B) is ethyl acrylate.

6. A polymer of claim 1 where the amount of the carboxylic acid monomer (A) ranges from about 25 weight percent to about 60 weight percent.

7. A polymer of claim 1 where m is 0 and R is methyl.

8. A polymer of claim 7 where n ranges from 6–50.

9. A polymer of claim 1 comprising:
A. about 30–55 weight percent of methacrylic acid, acrylic acid or mixtures thereof with fumaric or itaconic acid;
B. about 35–70 weight percent of ethyl acrylate or mixtures thereof with styrene, 2-hydroxyethyl acrylate, acrylonitrile, vinyl chloride or vinyl acetate; and
C. about 1–20 weight percent of the ethylenically unsaturated biphilic monomer of claim 1.

10. The polymer of claim 1 comprising:
A. about 30–45 weight percent of methacrylic acid;
B. about 50–70 weight percent of ethyl acrylate; and
C. about 1–12 weight percent of the compound of Formula I.

11. A polymer of claim 1 having an average particle size of about 500–3000 A and a Brookfield viscosity of about 50–50,000 cps as a 1 percent aqueous solution in ammonium salt form at pH 9.0 and 25° C.

12. A liquid aqueous colloidal dispersion useful as a pH responsive polymeric thickener for aqueous compositions and containing about 10–50 weight percent of the polymer of claim 6 and having a pH of about 2.5–5.0.

13. The liquid aqueous colloidal dispersion of claim 12 where the polymer consists essentially of:
A. about 30–45 weight percent of methacrylic acid;
B. about 50–70 weight percent of ethyl acrylate; and
C. about 1–12 weight percent of the compound of Formula I where m is 0 and n is about 6–40.

14. A process for making the liquid aqueous colloidal dispersion of claim 11 comprising emulsion copolymerizing the monomeric mixture at a pH of about 2.5–5.0 in the presence of a free-radical producing initiator at a temperature between about 60°–90° C.

15. A process of claim 14 wherein the emulsion copolymerization gives a polymer having an average particle size of about 500–3000 A and a Brookfield viscosity of about 50–50,000 cps as a 1 percent aqueous solution in ammonium salt form at pH 9.0 and 25° C.

16. A process of claim 13 wherein the monomeric mixture comprises:
A. about 30–45 weight percent of methacrylic acid;
B. about 50–70 weight percent of ethyl acrylate or a mixture thereof with styrene, 2-hydroxyethyl acrylate, acrylonitrile, vinyl chloride, or vinyl acetate; and
C. about 1–12 weight percent of the Compound of Formula I where m is 0 and n is about 6–100.

17. A thickened aqueous composition having a pH within the range of about 6.5–11.0 comprising an aqueous composition containing a water-soluble or dispersible material and an effective amount of a liquid emulsion polymer of claim 1.

18. A thickened aqueous composition of claim 16 wherein the aqueous composition is a colloidal dispersion of a water-insoluble polymer.

19. The thickened aqueous composition of claim 16 wherein the liquid emulsion polymer comprising:
A. about 30–45 weight percent of methacrylic acid;
B. about 50–70 weight percent of ethyl acrylate; and
C. about 1–12 weight percent of the Compound of Formula I where m is 0 and n is about 6–40.

20. A process for making a thickened aqueous composition which comprises:
(1) blending with the aqueous composition a sufficient amount of the liquid emulsion polymer of claim 6 to thicken the aqueous coating composition and
(2) adjusting the pH of said blend within a range of about 6.5–11.0 as necessary to dissolve the emulsion polymer therein and thus thicken the aqueous composition.

21. The process of claim 20 wherein the aqueous composition is a colloidal dispersion of a water-insoluble polymer.

22. The process of claim 20 wherein the liquid emulsion polymer comprises:
A. about 30–45 weight percent of methacrylic acid;
B. about 50–70 weight percent of ethyl acrylate; and
C. about 1–12 weight percent of the Formula I where m is 0 and n is about 6–100.

* * * * *